United States Patent
Harris et al.

(10) Patent No.: US 6,495,527 B1
(45) Date of Patent: Dec. 17, 2002

(54) COMPLEX OF DNA AND MICROPARTICLE OF DEFATTED LIPID-BINDING PROTEIN FOR GENE THERAPY

(75) Inventors: Roy Harris, Nottingham (GB); Nicholas David Osborne, Nottingham (GB)

(73) Assignee: Quadrant Healthcare, Ltd. (GB)

( * ) Notice: Subject to any disclaimer, the term of this patent is extended or adjusted under 35 U.S.C. 154(b) by 0 days.

(21) Appl. No.: 09/230,113

(22) PCT Filed: Jul. 22, 1997

(86) PCT No.: PCT/GB97/01970

§ 371 (c)(1), (2), (4) Date: Jan. 22, 1999

(87) PCT Pub. No.: WO98/03159

PCT Pub. Date: Jan. 29, 1998

(30) Foreign Application Priority Data

Jul. 23, 1996 (GB) ............................................. 9615435

(51) Int. Cl.[7] ...................... A61K 31/7088; A61K 9/14; A61K 38/00; C08H 1/00; C12N 11/02
(52) U.S. Cl. ......................... 514/44; 424/489; 435/177; 514/2; 530/402; 530/812
(58) Field of Search .................. 514/2, 44; 530/402, 530/812; 424/489; 435/177

(56) References Cited

U.S. PATENT DOCUMENTS

| | | | | |
|---|---|---|---|---|
| 4,094,965 A | * | 6/1978 | Layne et al. ................ | 424/1.5 |
| 4,720,385 A | * | 1/1988 | Lembach ..................... | 424/86 |
| 4,943,527 A | * | 7/1990 | Protter et al. ............... | 435/69.6 |
| 5,725,804 A | * | 3/1998 | Yen ............................ | 252/314 |

FOREIGN PATENT DOCUMENTS

| | | |
|---|---|---|
| WO | 9218164 | 10/1992 |
| WO | 9609814 | 4/1996 |
| WO | 9618388 | 6/1996 |

* cited by examiner

Primary Examiner—David M. Naff
(74) Attorney, Agent, or Firm—Saliwanchik, Lloyd & Saliwanchik

(57) ABSTRACT

Removal of lipid from lipid-bound protein such as human serum albumin to produce defatted protein enhances ability of the protein to bind therapeutic agents for use as a carrier for the therapeutic agent. The defatted protein may be reloaded with cationic and/or anionic lipids such as fatty acids, e.g. DC-Chol, to modify charge, hydrophilicity or hydrophobicity of the defatted protein to further enhance ability of the defatted protein to bind a therapeutic agent. A reloaded lipid itself may be a therapeutic agent. The defatted protein may be produced as microparticles by spray-drying. Defatting can be achieved by removing fatty acids with acidified activated charcoal, or by solvent extraction. A complex of DNA and a microparticle of defatted protein containing a cationic or anionic lipid molecule can be used for gene therapy. Defatted albumin may be reloaded with aminocaprylic acid to provide a microparticle for binding DNA for parenteral delivery. Microparticles of defatted protein having a modified predetermined fatty acid profile may be used as an enhanced ultrasound contrast agent.

3 Claims, No Drawings

COMPLEX OF DNA AND MICROPARTICLE OF DEFATTED LIPID-BINDING PROTEIN FOR GENE THERAPY

FIELD OF THE INVENTION

This invention relates to lipid-binding proteins such as defatted albumin, especially as a spray-dried product, and to their therapeutic and diagnostic use. More particularly, the invention relates to microparticles that can be used as carriers in therapy, e.g. gene therapy, and to the combination of carrier and therapeutic agent.

BACKGROUND OF THE INVENTION

Human serum albumin (HSA) is a protein whose production in the form of microparticles having a size suitable for use in therapy by parenteral administration or by inhalation, alone or as a carrier for an active agent, e.g. in a metered dose inhaler, is disclosed in WO-A-9609814 and in WO-A-9618388. The HSA may be used as such or as a carrier for a desired active agent, since appropriate spray-drying conditions do not denature the protein or essentially reduce the existence of groups available for binding.

As described in WO-A-9218164, albumin microparticles may be produced in soluble form and then stabilised, for use as diagnostic agents. WO-A-9618388 discloses that such products can be conjugated to therapeutic agents. WO-9609814 discloses that the soluble microparticles are not denaturated, and therefore retain therapeutic utility.

HSA is known to bind a wide range of ligands including drugs, dyes, toxic compounds (e.g. bilirubin) and hydrophobic molecules such as fatty acids. Fatty acid transport is possibly one of the most important functions of HSA. A loading of up to two molecules of lipid is considered normal with a high turnover rate. HSA has the ability to bind fatty acids with high affinity, and this appears to increase with the increasing length of the fatty acid chain. Very high affinities ($K_a=10^7-10^9$) have been reported for long chain fatty acids. HSA is capable of binding up to 6–7 molecules of fatty acid/molecules of protein with moderate to high affinities. Low affinity binding of fatty acids, in numbers as high as 60 molecules of fatty acids/HSA molecule, has been reported.

Fatty acids give added stability to the HSA molecule, and the conformation and subsequent ability to bind ligands are affected by the amount and type of fatty acid bound. Fatty acids also protect against thermal denaturation and the ability of HSA to recover from thermal shock. Long chain fatty acids appear to be better than shorter chain fatty acids. See Brown and Shockley (1982), in "Lipid Protein Interactions", Ed. P. C. Jost and O. H. Griffith, vol 1, pp 25–68, John Wiley, NY; Kragh-Hanson (1990), Danish Medical Bulletin 37:57–84; and Carter and Ho (1994), Advances In Protein Chemistry 45:153–203.

SUMMARY OF THE INVENTION

It has now been discovered that lipid-bound proteins such as albumin may associate only weakly with DNA, but that lipid-binding proteins such as defatted albumin, provided as microparticles, have surprisingly enhanced association with DNA. Without wishing to be bound by theory, we note that short-chain fatty acids (e.g. octanoate) are not removed by long-chain fatty acids, suggesting that higher affinity short-chain sites occupy the lower affinity long-chain sites on, say, HSA. Defatting of HSA may therefore make available some or all of the 6–7 high affinity long-chain fatty acid sites and further high affinity short-chain sites.

The ability of lipid-binding proteins such as defatted HSA to associate with DNA may be further enhanced by the addition of a cationic molecule (DNA being anionic). It is a feature of this invention that defatted albumins can be loaded with a wide range of fatty acids, e.g. DC-Chol, or other ligands which would otherwise be inhibited by the presence of the naturally-bound fatty acids. The removal of fatty acids liberates not only these sites but also makes available binding sites for aspirin or other drugs. The removal of a mixed population of fatty acids (and probably other ligands) allows the reloading of specific fatty acids, drugs or intermediate ligands to assist in the stability, conformational structure and/or binding capabilities of microparticles of defatted albumin. The reloading of, for example, aminocaprylic acid may be achieved prior to or after spray-drying of defatted albumin, to give a cationic capsule for DNA binding and parenteral delivery. The microparticles may also be loaded, at the time of administration, with a drug-bound fatty acid (ligand) complex, potentially improving usage, storage, stability and applications.

Further, microparticles of the invention having a modified, predetermined fatty acid profile may be used as enhanced ultrasound contrast agents.

DESCRIPTION OF THE INVENTION

Microparticles according to the invention are obtainable by spray-drying. Suitable conditions are described in WO-A-9218164, WO-A-9609814 and WO-A-9618388. These publications also describe relevant parameters of the microparticles, as regards formulation, size, size distribution etc. These parameters are also preferred for microparticles of this invention. Size and size distribution may be less critical than has been described in the given particles for, say, administration to the alveoli. Microparticles of this invention may be nanoparticles or larger, e.g. up to 50 $\mu$m in diameter.

The microparticles may comprise additional components adapted for a particular use. For example, lipid may enhance cell membrane interaction and thus enhance uptake. The lipid itself or any additional component may be introduced by co-spray-drying or by modification of the formed microparticles, before or after stabilisation.

An additional component may be introduced by co-spray-drying or by modification of the formed microparticles, before or after stabilisation.

For use in this invention, a lipid-bound protein such as albumin is defatted. This may be achieved, i.e. fatty acids may be removed, by using acidified activated charcoal, as described by Chen, J. Biol. Chem. 242:173–181 (1967). The charcoal should be washed. Alternatively, solvent extraction may be used.

An albumin is the preferred lipid-binding protein for use in this invention, e.g. in soluble or microparticulate form. The albumin may be naturally-occurring or recombinant. For the purpose of illustration only, the invention will be described below with reference to HSA.

Clinical grade HSA is normally formulated with octanoate (in the presence or absence of tryptophanamide). After removal of this, and defatting, a cationic version of this lipid (e.g. aminocaprylic or aminocaproic acid) can be bound to HSA or HSA microcapsules. Other cationic lipids can also be loaded, pre- or post-spray-drying, producing a vehicle for parenteral delivery of non-viral gene vectors. The utility of albumin microparticles, as a vehicle for gene therapy, and suitable constituents and conditions, are disclosed in PCT/GB97/00953, the contents of which are incorporated herein by reference.

Cationic and/or anionic lipids or ligands that bind to free fatty acid-binding sites on HSA can be used to modify the charge and hydrophilicity or hydrophobicity of the microcapsule. This may be advantageous for the targeting of microcapsules for delivery of cytotoxic and other drugs to specific organs such as lung, liver, spleen etc. For example, by appropriate charge modification, a product of this invention may be adapted to bypass the liver and be transported to the lung.

The reloading of, for example, long-chain fatty acids may lead to an altered but more stable configuration of the protein. The molecules may be modified accordingly, to produce microcapsules with modified shell structure relative to the stabilised/cross-linked products described in WO-A-9218164 (available from Andaris Limited under the trade name Quantison), for improved drug delivery and also for better echogenicity for imaging.

In a therapeutic product of the invention, a therapeutic agent may be complexed with or loaded directly onto defatted HSA microparticles. Alternatively, a fatty acid-agent complex may be formed, e.g. by covalent binding, and used to reload the defatted microparticles.

The lipid that is loaded may itself be a therapeutic agent. For example, the invention is of utility as a vaccine delivery system, e.g. using a lipopeptide. The inclusion of a polycationic or polyanionic tail on the end of a peptide allows the loading of microcapsules with proteinaceous material, and thus provides a means of delivering antigenic peptides. A suitable lipopeptide is described by Allsopp et al, Eur. J. Immunol. (1996) 26:1951–9, where a lipid-tailed peptide induced high levels of cytotoxic T lymphocytes.

The amount of therapeutic agent that is used according to the invention, and its formulation (e.g. with a suitable diluent or carrier) and administration, may be conventional. These factors can readily be determined by one of ordinary skill in the art, depending on the nature and degree of the desired effect.

The following Examples illustrate the invention (and also provide information for the purpose of comparison).

EXAMPLES 1 TO 3 AND EXAMPLE A (COMPARATIVE)

Microcapsules were prepared under the same conditions from HSA (Example A), defatted HSA (Example 1) and aminocaprylic acid or lysine with defatted HSA (Examples 2 and 3, respectively). The DNA-binding properties of each product were investigated.

Triplicate aliquots of each product (5 mg microcapsules) were incubated with DNA (2 mg/ml aqueous, Sigma herring) at room temperature for 16 hours. The uptake of DNA by the microcapsules was determined spectrophotometrically. Results are given in Table 1.

TABLE 1

| Example | Mean Particle Diameter ($\mu$m) | DNA Association (% w/w) |
|---|---|---|
| 1 | 4.34 | 4.5 |
| 2 | 3.15 | 7.8 |
| 3 | 3.96 | 5.9 |
| A | 3.04 | 0.8 |

Surprisingly, defatted HSA microcapsules bound 4.5% w/w DNA. This was much greater than expected. Aminocaprylic acid and lysine both enhanced the DNA association, giving loadings of 7.8% and 5.9% w/w respectively. Control HSA microcapsules only weakly associated with DNA, as expected.

The concentration of aminodaprylic acid loaded onto defatted HSA in Example 2 was determined by amino-acid analysis using pre-column derivatisation with o-phthaldialdehyde reagent (OPA). A series of standards was prepared by derivatising aminocaprylic acid with OPA.

Calculations have determined that the loading of aminocaprylic acid onto defatted HSA was 0.87 $\mu$g per 1 mg HSA microcapsules, i.e., 0.087% w/w. This is equivalent to 5.4 nmoles aminocaprylic acid per mg HSA (or per 15 nmoles protein).

EXAMPLE 4

261 g activated charcoal (Sigma, 73HO369) was resuspended in 2500 ml purified water. The resultant suspension was sieved (0.45 $\mu$m) and washed with 15 l purified water. The washed charcoal was spread evenly over a metal tray and dried in the laboratory oven for 8 hours at 65° C.

8000 ml of HSA (Armour US, N28510, 5%) was divided into 1000 ml glass bottles. 31.25 g of the washed charcoal was added to each bottle. The pH of each suspension was lowered to 3.0 using concentrated hydrochloric acid. The bottles were then placed in an ice bath and were vigorously shaken every 10 minutes. After 90 minutes, the bottles were removed from the ice bath.

The charcoal was removed from the solution by centrifugation at 10,000 rpm for 20 minutes. The supernatants were sterile-filtered (0.2 $\mu$m). The defatted HSA solution was then diafiltered with 5 volumes purified water before being concentrated to 250 mg/ml. The pH was adjusted to 7.0 before the concentration process. The concentrated defatted HSA was sterile-filtered and stored at 4° C.

A feedstock for spray-drying was prepared, using the defatted HSA in a 100 mg/ml concentration, ethanol at 25% of the feedstock volume, and purified water. The Niro Mobile Minor was employed under the following conditions:

| Inlet Temperature | 220° C. |
|---|---|
| Outlet Temperature | 99° C. |
| Atomisation Type | 2 fluid nozzle |
| Atomisation Pressure | 7.5 barg |

The resultant microcapsules were stabilised (176° C., 55 minutes) and deagglomerated, under conditions as described in WO-A-9218164.

EXAMPLES 5 AND 6

Two fatty acids of different chain lengths were selected: DC-Chol (example 5) and amino-n-caproic acid (Example 6). A 2% loading of each lipid onto the microcapsule was attempted.

300 mg deagglomerated defatted HSA microcapsules (containing 100 mg protein and 200 mg mannitol excipient) were washed and centrifuged (3000 rpm, 3 minutes). The pellet was resuspended in 5 ml of the respective lipid solution (containing 2 mg lipid). The DC-Chol required dissolution in chloroform before reconstitution in 5 ml purified water.

The solutions were left for 30 minutes on the roller mixer, after which the solutions were centrifuged (3000 rpm, 10 minutes). The supernatants were discarded whilst the pellets were resuspended in 5 ml mannitol solution (50.8 mg/ml) before freeze-drying.

Acoustic Scattering

The microcapsules from Examples 4, 5 and 6 were assessed for their suitability as enhanced ultrasound contrast agents. The assessment of their acoustic scattering properties was carried out using two techniques with a commercially-available ultrasound scanner equipped with a 3.5 MHz transducer (Model SONOS 1000, Hewlett Packard).

For the first assessment, a background measurement was taken of a stirred 400 ml polypropylene test beaker containing 350 ml of gas-equilibrated water at ambient temperature with the transducer face immersed to a depth of 1.5 cm.

The following instrument settings were used:

| | |
|---|---|
| Transmit = | 60 dB |
| Total Gain Controls = | 128 |
| Compression = | 128 |
| Depth = | 8 cm |
| Persistence = | 0 |

5 mg of the microcapsules evenly dispersed in 250 μl of water were then carefully added to the stirred beaker and a further measurement made. The measurements were assessed by using image analysis to give a numerical value to the brightness seen on the monitor, known as visual display units (VDUs). When the background is subtracted, the relative echogenicity of the microcapsules can be found. All measurements were repeated in triplicate and are shown in Table 2. It can be observed that DC-Chol-loaded microcapsules exhibit enhanced scattering properties.

TABLE 2

| | Echogenicity (VDUs) | | |
|---|---|---|---|
| Sample | Assay 1 | Assay 2 | Assay 3 |
| Example 4 | 39 | 39 | 41 |
| Example 5 | 63 | 66 | 61 |
| Example 6 | 32 | 34 | 35 |

The second assessment of echogenicity used a similar arrangement to the first, with a larger stirred polypropylene test beaker containing 1000 ml of gas-equilibrated water at 37° C. Again, a background measurement was taken with the following instrument settings, to ensure that no significant background reading was present.

| | |
|---|---|
| Transmit = | 128 dB |
| Total Gain Controls = | 128 |
| Compression = | 1 |
| Depth = | 8 cm |
| Persistence = | 0 |

4 mg of the microcapsules evenly dispersed in 200 μl of water were then carefully added to the stirred beaker, and further measurements made as the transmit power was incrementally increased from 80 to 128 dB. Again, the measurements were assessed by using image analysis, to give a numerical value to the brightness. The results are shown in Table 3. It can be seen that again the DC-Chol-loaded microcapsules exhibit enhanced scattering properties at lower transmit power levels.

TABLE 3

| Transmit Power (dB) | Echogenicity (VDUs) | | |
|---|---|---|---|
| | Example 4 | Example 5 | Example 6 |
| 80 | 2 | 44 | 2 |
| 85 | 3 | 38 | 3 |
| 90 | 7 | 51 | 3 |
| 92 | 9 | 63 | 4 |
| 94 | 11 | 69 | 5 |
| 96 | 19 | 85 | 7 |
| 98 | 26 | 86 | 9 |
| 100 | 38 | 110 | 14 |
| 102 | 43 | 113 | 23 |
| 104 | 67 | 130 | 35 |
| 106 | 92 | 147 | 64 |
| 108 | 124 | 149 | 95 |
| 110 | 146 | 150 | 132 |
| 115 | 150 | 151 | 152 |
| 128 | 147 | 150 | 148 |

EXAMPLES 7 TO 9

DNA was bound to each of the microcapsule batches of Examples 4–6, and also to a control. Four aliquots of 15 mg of each of the four batches were weighed out, each aliquot containing 5 mg microcapsules. To 3 of the 4 aliquots, 0.5 ml DNA solution (2 mg/ml, Herring Testes) was added, and the resultant solutions were placed on a shaker table for 16 hours at room temperature. The fourth aliquot for each batch was retained as a control. An aliquot of the DNA solution was left for 16 hours as a control.

After 16 hours, the samples were centrifuged (15,000 rpm, 2 minutes), and the supernatants were diluted 1:40 and filtered. The samples were then scanned at 400–190 nm using the UV/VIS spectrophotometer. The results are given in Table 4.

TABLE 4

| Sample | Microcapsule Count per mg | DNA Association (μg/mg Capsules) |
|---|---|---|
| Control | $2.5 \times 10^6$ | — |
| Example 7 | $1.56 \times 10^7$ | 32 (3.2% w/w) |
| Example 8 | $1.56 \times 10^7$ | 77.0 (7.7% w/w) |
| Example 9 | $1.56 \times 10^7$ | 100.6 (10.06% w/w) |

EXAMPLE 10

The microcapsules of Example 5, i.e. comprising the cationic lipid DC-Chol, or 3β-[N-(N',N'-dimethylaminoethane)carbamoyl]cholesterol, were again bound to DNA. The DNA was the commercially-available luciferase reporter plasmid pGL3-control (Promega). This plasmid contains the SV40 promoter and enhancer driving the expression of the firefly luciferase gene. Upon transfection of this plasmid into mammalian cells, transcription of the luciferase gene at high levels leads to a high level of luciferase enzyme expressed within the cells. The activity of the luciferase enzyme can be readily assayed in cell lysates, using commercially-available reagents. Since mammalian cells possess no endogenous luciferase gene, enzyme activity in transfected cells can be correlated with the efficiency of transfection of the pGL3 plasmid.

The procedures for binding DNA onto the cationic lipid containing microcapsules and the subsequent gene transfection experiments were as follows:

20 mg microcapsules were incubated with 20 μg pGL3 plasmid in PBS buffer for 2 hours. The DNA-loaded microcapsules were washed and resuspended in Optimem (cell culture medium) and then incubated with A549 (human lung carcinoma) and HeLa (human cervical epithelial carcinoma) cells at $5 \times 10^5$ per well for between 2 and 28 hours at 37° C. At the end of the transfection, the cells were returned to standard culture medium and harvested 28 hours from the start of the experiment. Cell lysates were prepared and luciferase activity measured using standard protocols.

Transfection was observed, at a level approx. 1000-fold higher than for a negative control. Maximal DNA uptake was reached between 2 and 6 h, suggesting that there is no need for longer exposure times.

What is claimed is:

1. A complex of DNA and a microparticle, wherein said microparticle comprises a lipid-binding protein and a cationic or anionic lipid molecule, wherein said lipid-binding protein is obtained by defatting a lipid-bound protein of naturally-bound fatty acids.

2. The complex according to claim 1, wherein said lipid molecule is cationic and complexes with said DNA.

3. A method for providing gene therapy to a person or animal, said method comprising administering a therapeutic amount of a complex of DNA and a microparticle, wherein said microparticle comprises a lipid-binding protein and a cationic or anionic lipid molecule, wherein said lipid-binding protein is obtained by defatting a lipid-bound protein of naturally-bound fatty acids.

* * * * *